US012656324B2

(12) United States Patent
Hochstetler

(10) Patent No.: US 12,656,324 B2
(45) Date of Patent: Jun. 16, 2026

(54) WATER METER AND ASSOCIATED WATER SYSTEM USING THE SAME

(71) Applicant: Mervin C. Hochstetler, Holland, MI (US)

(72) Inventor: Mervin C. Hochstetler, Holland, MI (US)

( * ) Notice: Subject to any disclaimer, the term of this patent is extended or adjusted under 35 U.S.C. 154(b) by 432 days.

(21) Appl. No.: 18/122,757

(22) Filed: Mar. 17, 2023

(65) Prior Publication Data

US 2024/0310349 A1 Sep. 19, 2024

(51) Int. Cl.
| | |
|---|---|
| *G01N 33/18* | (2006.01) |
| *G01F 15/06* | (2022.01) |
| *G01F 15/063* | (2022.01) |
| *G06Q 50/06* | (2024.01) |

(52) U.S. Cl.
CPC ........... *G01N 33/18* (2013.01); *G01F 15/063* (2013.01); *G06Q 50/06* (2013.01)

(58) Field of Classification Search
None
See application file for complete search history.

(56) References Cited

U.S. PATENT DOCUMENTS

| | | | |
|---|---|---|---|
| 5,636,653 | A | 6/1997 | Titus |
| 5,892,158 | A | 4/1999 | Franklin et al. |
| 5,971,011 | A | 10/1999 | Price |
| 7,360,413 | B2 | 4/2008 | Jeffries et al. |
| 7,526,365 | B1 | 4/2009 | Frerich et al. |

| | | | | |
|---|---|---|---|---|
| 8,347,427 | B2 | 1/2013 | Kicpera | |
| 8,531,303 | B2 * | 9/2013 | Pham | C02F 1/006 |
| | | | | 340/603 |
| 8,887,324 | B2 | 11/2014 | Klicpera | |
| 8,994,551 | B2 | 3/2015 | Pitchford et al. | |
| 9,912,732 | B2 | 3/2018 | Romney et al. | |
| 10,410,501 | B2 * | 9/2019 | Klicpera | F16K 31/02 |
| 10,809,175 | B1 * | 10/2020 | Ayadat | G01N 15/0826 |
| 10,965,488 | B2 | 3/2021 | Wright et al. | |
| 11,029,196 | B2 | 6/2021 | Wright et al. | |
| 11,095,960 | B2 * | 8/2021 | Klicpera | H04L 12/2827 |
| 11,407,653 | B2 | 8/2022 | Yates | |
| 2006/0113537 | A1 * | 6/2006 | Krulevitch | H01L 21/6835 |
| | | | | 257/E25.031 |

(Continued)

FOREIGN PATENT DOCUMENTS

CN        214504599 U   * 10/2021   ........... G01F 15/063

OTHER PUBLICATIONS

Brodie et al., "An Overview of Tools for Assessing Groundwater-Surface Water Connectivity", 2007, Commonwealth of Australia. (Year: 2007).*

(Continued)

*Primary Examiner* — Mohammad Ali
*Assistant Examiner* — Kelvin Booker
(74) *Attorney, Agent, or Firm* — King & Partners, PLC

(57) ABSTRACT

A smart water meter, including: a water flow measuring assembly; one or more water parameter sensors; a data transmission assembly; and wherein the smart water meter validates, and, in turn, provides peace of mind to a consumer that there are no water leaks and/or that the water utilized is safe and within predetermined parameters (e.g., free from lead, mercury, heavy metals, hydrocarbons, pesticides, herbicides, fungicides and/or PFAS).

17 Claims, 4 Drawing Sheets

(56)            References Cited

U.S. PATENT DOCUMENTS

| | | | |
|---|---|---|---|
| 2008/0092965 A1* | 4/2008 | Hymes | A01K 7/02 |
| | | | 137/624.12 |
| 2009/0032446 A1* | 2/2009 | Wiemers | B01D 19/0036 |
| | | | 210/85 |
| 2011/0035063 A1 | 2/2011 | Palayur | |
| 2012/0152374 A1* | 6/2012 | Hymes | A01K 7/02 |
| | | | 137/392 |
| 2014/0018965 A1 | 1/2014 | Pearson et al. | |
| 2015/0192933 A1* | 7/2015 | Hymes | G05D 9/12 |
| | | | 137/386 |
| 2015/0253163 A1* | 9/2015 | Ruiz Cortez | G01F 1/075 |
| | | | 73/198 |
| 2016/0091432 A1* | 3/2016 | Clark | G01N 21/8507 |
| | | | 422/429 |
| 2017/0184417 A1* | 6/2017 | Pedreiro | G01D 4/002 |
| 2017/0335550 A1 | 11/2017 | Sterling et al. | |
| 2018/0188093 A1* | 7/2018 | Danlogo | G01F 15/068 |
| 2018/0283977 A1* | 10/2018 | DeVerse | G16Z 99/00 |
| 2018/0292248 A1* | 10/2018 | Heizenroeder | G01F 15/063 |
| 2018/0347157 A1* | 12/2018 | Brotherton | E03B 7/072 |
| 2019/0003976 A1* | 1/2019 | Clark | G01N 21/15 |
| 2019/0025150 A1* | 1/2019 | Picardi | G05B 23/0218 |
| 2019/0086233 A1* | 3/2019 | Comfort | G01F 15/063 |
| 2019/0234786 A1 | 8/2019 | Klicpera | |
| 2019/0323919 A1* | 10/2019 | Fung-A Wing | E03B 7/07 |
| 2020/0121715 A1* | 4/2020 | Bishop | A61K 33/00 |
| 2021/0125486 A1* | 4/2021 | Shabbir | G08B 21/20 |
| 2021/0381207 A1* | 12/2021 | Brotherton | E03B 7/071 |
| 2022/0228901 A1* | 7/2022 | Mackie | G01F 15/185 |
| 2022/0276114 A1* | 9/2022 | Mahdjoubi Namin | |
| | | | G01M 3/2815 |
| 2025/0067615 A1* | 2/2025 | Larsen | G01M 3/002 |

OTHER PUBLICATIONS

Zhang et al., "Using Water Level Responses to Atmospheric Pressure Variations to Measure and Monitor Vertical Leakage Through Confining Units, With Application to the Jurassic Shaximiao Crust, China", Apr. 2024, Advancing Earth and Space Sciences. (Year: 2024).*

Awwad et al., "Remote Thermal Water Leakage Sensor With a Laser Communication System", Aug. 2020, IEEE Access. (Year: 2020).*
Michalski et al., "First field application of temperature sensor modules for groundwater flow detection near borehole heat exchanger ", 2019, Geothermal Energy. (Year: 2019).*
Munn et al., "Measuring Fracture Flow Changes in a Bedrock Aquifer Due to Open Hole and Pumped Conditions Using Active Distributed Temperature Sensing", Jan. 2020, Advancing Earth and Space Sciences. (Year: 2020).*
Wang et al., "Characterization of horizontal transmissivity anisotropy using cross-hole slug tests", Dec. 2017, Journal of Hydrology 564 (2018) 89-98. (Year: 2017).*
Brunone et al., "Design criteria and performance analysis of a smart portable device for leak detection in water transmission mains", Feb. 2021, Measurement 183 (2021) 109844. (Year: 2021).*
Willmann et al., "On the meaning of the transmissivity values obtained from recovery tests", Dec. 2005, Hydrogeology Journal (2007) 15: 833-842. (Year: 2005).*
Yamano et al., "Long-term monitoring of the temperature profile in a deep borehole: Temperature variations associated with water injection experiments and natural groundwater discharge", Jan. 2004, Physics of the Earth and Planetary Interiors 152 (2005) 326-334. (Year: 2004).*
Michalski et al., "Temperature sensor module for groundwater flow detection around borehole heat exchangers", 2018, Geotherm Energy (2018) 6:15. (Year: 2018).*
Nemeth et al., "Evaluation of the use of reach transmissivity to quantify exchange between groundwater and surface water", Mar. 2002, Journal of Hydrology 274 (2003) 145-159. (Year: 2002).*
Almazyad et al., "A Proposed Scalable Design and Simulation of Wireless Sensor Network-Based Long-Distance Water Pipeline Leakage Monitoring System", Oct. 2013, Sensors 2014, 14, 3557-3577. (Year: 2013).*
Rahmat et al., "Water Pipeline Monitoring and Leak Detection using Flow Liquid Meter Sensor", Journal of Physics: Conference Series 755. (Year: 2016).*
Khan et al., "Performance assessment of leak detection failure sensors used in a water distribution system", Journal of Water Supply: Research and Technology, Aqua, 54.1, 2005. (Year: 2005).*

* cited by examiner

WATER METER AND ASSOCIATED WATER SYSTEM USING THE SAME

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A SEQUENCE LISTING

Not applicable.

BACKGROUND OF THE INVENTION

1. Field of the Invention

The present invention relates in general to water meters, and, more particularly, to smart water meters that continuously monitor water consumption and quality in real time so that a consumer has peace of mind knowing that there are no water leaks and that the water being utilized is safe and within predetermined parameters. The smart water meters of the present invention are also capable of recording, storing, and reporting historical water quality data. The smart water meters of the present invention are further capable of isolating and alerting the consumer and/or municipality if a water leak is detected and/or the water quality is outside of predetermined, safe parameters-such as the presence of lead, mercury, heavy metals, hydrocarbons, pesticides, herbicides, fungicides and per- and/or polyfluoroalkyl substances (PFAS) found in, for example, drinking water. Water quality can be adversely affected by natural disasters, acts of God, government and/or the private sector.

The present invention is also directed to smart water systems that utilize smart water meters capable of diverting unsafe water from a consumer to a reservoir and/or sewer.

2. Background Art

Water meters and associated water systems have been known in the art for years and are the subject of a plurality of patents and/or publications, including: U.S. Pat. No. 11,407,653 entitled "Method, System and Apparatus for Monitoring and Controlling Water Quality and Flow," U.S. Pat. No. 11,029,196 entitled "Vibration Sensor for Fluid Leak Detection," U.S. Pat. No. 10,965,488 entitled "System and Method for Monitoring a Property," U.S. Pat. No. 8,994,551 entitled "Systems and Methods for Remote Utility Metering and Meter Monitoring," U.S. Pat. No. 8,887,324 entitled "Water Use Monitoring Apparatus," U.S. Pat. No. 8,347,427 entitled "Water Use Monitoring Apparatus," U.S. Pat. No. 5,636,653 entitled "Fluid Metering Apparatus and Method," United States Patent Application Publication Number 2019/0234786 entitled "Water Meter and Leak Detection System," United States Patent Application Publication Number 2017/0335550 entitled "Interactive Water Monitoring System," and United States Patent Application Publication Number 2011/0035063 entitled "Water Management System"—all of which are hereby incorporated herein by reference in their entirety including all references cited therein.

U.S. Pat. No. 11,407,653 appears to disclose a water quality and flow monitoring and control apparatus, method and system that are installed at an end user location and capable of monitoring one or more of the following water quality parameters: microorganisms (including *E. coli*), mineral or other ion concentration, pH, temperature, and turbidity. The system also has a water meter that detects the flow of water and has a valve to shut the flow of water off upon detecting a fault condition such as a leak.

U.S. Pat. No. 11,029,196 appears to disclose a vibration sensor. The vibration sensor comprises: a sensor base to couple to a vibration source; a piezoelectric transducer coupled on a first side of the transducer to the sensor base; at least one conductor coupled to the piezoelectric transducer; and a seismic weight positioned on a second side of the piezoelectric transducer; wherein the sensor base, the piezoelectric transducer and the seismic weight are aligned along an axis and arranged so that relative movement between the sensor base and the seismic weight arising from the vibration source causes a current to be generated in the piezoelectric transducer and an output signal corresponding to the generated current is detectable on the at least one conductor.

U.S. Pat. No. 10,965,488 appears to disclose systems and methods for monitoring a property using a system of sensor units in one or more premises on the property that can interface with respective utilities entering the premises or being generated by appliances on the premises with a minimal of effort and without requiring modification of the utility's equipment or the appliance. The systems and methods are connectable to a cloud-based monitoring, analytics and notification system via a long-range network connection directly from one or more of the sensor units. The system of sensors can also incorporate primary and secondary units with at least one primary unit capable of communicating directly to the cloud-based system/server via a long-range connection with the secondary units sending data to the cloud via the primary unit by communicating at the property via a short-range communication connection. There are also provided various sensor units for specifically monitoring water flow and water leakage, flooding, sump pump operability, levels within water softeners and other fluid containing vessels, electrical power usage, furnace operations, among others as described herein.

U.S. Pat. No. 8,994,551 appears to disclose a remote water meter monitoring system. A mesh network-type transceiver unit is coupled to a water meter housing having a water counting mechanism inside to transmit water consumption information as well as other sensor information, such as backflow detection, water pressure, and water metrics (e.g., residual chlorine and temperature) to a central server system via a bridge device and a corresponding mesh network. Mechanical energy from the water flowing through the water meter housing is converted to electrical energy via an energy conversion unit. An electrically powered shut off valve is remote addressable via the transceiver unit.

U.S. Pat. No. 8,887,324 appears to disclose a water use and/or a water energy use monitoring apparatus that is affixed to the hot and cold-water supply piping for continuously (or on demand) monitoring displaying the water and water energy (hot vs. ambient) use within a residential or commercial building. A first wire or wireless means is incorporated to communicate with a remote display for viewing by the owner of a commercial building or occupier/resident of a home. A second optional wire or wireless means can be incorporated that can be monitored by civil, commercial, governmental or municipal operators or agencies, using a remote display and/or recorder means or by a secure wire or wireless communication network (e.g., cell phone technology communication means). A third wireless means communicates water parameter data utilizing typical cell tower technology and/or mesh network technology. The water use monitor apparatus includes a power generation, a microprocessor, temperature and water flow sensors, optional water quality sensors, timing circuits, wireless circuitry, and a display means. A first wired or wireless means is designed to electronically communicate water use and water energy use information to a remotely located display for convenient observation by a commercial operator or occupier, or resident. An optional second wireless means is designed to electronically communicate water and/or water energy use information to governmental or municipal operators or agencies.

U.S. Pat. No. 8,347,427 appears to disclose a water use and/or a water energy use monitoring apparatus that is affixed to the hot and cold main water supply piping for continuously (or on demand) monitoring and displaying the water use within a residential or commercial building. A first wire or wireless communication is incorporated to electronically communicate with a remote display for viewing by the owner of a commercial building or occupier/resident of a home. A second optional wire or wireless communication can be incorporated that can be monitored by civil, commercial, governmental or municipal operators or agencies, using a remote display and/or recorder or by a secure wire or wireless communication network (e.g., cell phone communication technology). A third wireless communication can be incorporated to electronically communicate water parameter data utilizing typical cell tower technology and/or mesh network technology.

U.S. Pat. No. 5,636,653 appears to disclose an apparatus and method for metering fluid flow. A fluid dispensing unit is coupled between a supply pipe and a demand pipe, and dispenses fluid received from the supply pipe to the demand pipe. The demand pipe is coupled to one or more fluid-expending appliances. The pressure of the fluid in the demand pipe is monitored by a fluid information unit. The fluid information unit and fluid dispensing unit cooperate to maintain the fluid flowing through the demand pipe at a substantially constant demand fluid pressure by monitoring fluid flowing through the demand pipe and actively dispensing fluid received from the supply pipe into the demand pipe to maintain the demand fluid pressure at a pre-established demand pressure level. The fluid information unit and fluid dispensing unit also cooperate to meter or measure the volume of fluid dispensed through the fluid dispensing unit. The fluid dispensing unit includes a controllable valve responsive to valve control signals produced by the fluid information unit. The volume of fluid dispensed through the valve is computed using the difference between the supply and demand fluid pressures and a duration of time during which the fluid is flowing through the valve. Alternatively, the volume of dispensed fluid is computed using the supply and demand fluid pressure difference and a characteristic duty cycle factor or characteristic flow factor of the valve.

United States Patent Application Publication Number 2019/0234786 appears to disclose a water meter and leak detection system that has a private or public property(ies) facility water supply interruption system. The system is comprised of a water meter collection node system with shut-off/on mechanism that has wireless Bluetooth, Bluetooth low energy, Zigbee, Z-wave LoRa, Wi-Fi, radio frequency and cellular technology with a private or corporate network, or internet connection that transfer water parameter data to a remote computer or server. Or the system can consist of a water meter collection node that communicates by Bluetooth, Bluetooth low energy, Zigbee, Z-wave LoRa, Wi-Fi, radio frequency and cellular technology with a data communication hub whereby the communication hub is in wired or wireless communication with an internet router that communicates with an internet connection, or with a private or commercial network system, to a remote computer/server or a cloud-computing commercial service.

United States Patent Application Publication Number 2017/0335550 appears to disclose an exemplary system for an interactive water supply management system for use in residential and commercial properties and a method of installation and use. In the preferred embodiment is a system comprising a water consumption sensor capable of being externally mounted to a water meter, circuitry for the collection of water consumption data, a communication system allowing two-way communication with a user and a water main valve shutoff. Remote vibration sensors on water pipes or acceleration sensors on manually articulated water valves provide feedback to the system to allow automatic identification of water consumed by each faucet or appliance. The communication system includes a means of two-way communication through the manipulation of the water flow rate by the water shut off valve or by a user.

United States Patent Application Publication Number 2011/0035063 appears to disclose a water consumption monitoring and control system comprised of a base unit, itself comprising a display and a data entry device, a microprocessor, a communication link to water meters, pressure sensors, temperature sensors, flush toilet vibration sensors and shut-off valves. In addition, the base unit has access to the Internet and can access a server which holds a database of water conservation information. This database includes watering advisories from the local government, and weather information from the weather office. The server runs an algorithm and generates control data which is sent to the base unit.

While the above-identified patents and publications do appear to disclose various water meters and water meter systems, their configurations remain non-desirous and/or problematic inasmuch as, among other things, none of the above-identified references appear to disclose a smart water meter that continuously monitors water quality in real time so that a consumer has peace of mind knowing the water being utilized is safe and within predetermined parameters. Moreover, none of the prior art water meters appear to be capable of recording, storing, and reporting historical water quality data. Nor do they appear capable of alerting the consumer and/or municipality if a water leak is detected and/or the water quality is outside of predetermined, safe parameters. Furthermore, none of the prior art smart water systems appear to be capable of diverting unsafe water from a consumer to a reservoir and/or sewer.

These and other objects of the present invention will become apparent in light of the present specification, claims, and drawings.

SUMMARY OF THE INVENTION

The following presents a simplified summary in order to provide a basic understanding of some aspects of the claimed subject matter. This summary is not an extensive overview, and is not intended to identify key/critical elements or to delineate the scope of the claimed subject matter.

Its purpose is to present some concepts in a simplified form as a prelude to the more detailed description that is presented later.

The present invention is directed to a smart water meter comprising, consisting essentially of and/or consisting of: (a) a water flow measuring assembly; (b) one or more water parameter sensors; (c) a data transmission assembly; and (d) wherein the smart water meter validates, and, in turn, provides peace of mind to a consumer that there are no water leaks and/or that the water utilized is safe (e.g., free from the presence of lead, mercury, heavy metals, hydrocarbons, pesticides, herbicides, fungicides and/or PFAS) and/or within predetermined parameters.

In a preferred embodiment of the present invention, the smart water meter records, stores, and reports historical water quality data, as well as water flow rates and water consumption over one or more periods of time.

In another preferred embodiment of the present invention, the smart water meter alerts the consumer and/or municipality if a water leak and/or water flow irregularity (e.g., backflow, clog, etcetera) is detected and/or if the water quality is outside of predetermined, safe parameters.

In yet another preferred embodiment of the present invention, the water flow measuring assembly comprises a housing, a water input, a water output, and a water flow measuring chamber.

In one preferred embodiment of the present invention, the water parameter sensor(s) measure water temperature.

In a preferred implementation of the present invention, the water parameter sensor(s) measure potential of hydrogen (pH).

In another preferred implementation of the present invention, the water parameter sensor(s) measure turbidity.

In yet another preferred implementation of the present invention, the water parameter sensor(s) measure transmissivity.

In a preferred aspect of the present invention, the water parameter sensor(s) measure conductance.

In a preferred embodiment of the present invention, the water parameter sensor(s) measure the concentration of dissolved oxygen in the water.

In another preferred embodiment of the present invention, the water parameter sensor(s) measure the concentration of blue-green algae (cyanobacteria) in the water.

In yet another preferred embodiment of the present invention, the water parameter sensor(s) measure the concentration of chlorophyll in the water.

In one preferred embodiment of the present invention, the water parameter sensor(s) measure the concentration of colored dissolved organic matter (CDOM) in the water.

In a preferred implementation of the present invention, the water parameter sensor(s) measure total cation, anion, and/or ion concentration.

In another preferred implementation of the present invention, the water parameter sensor(s) measure total hydrocarbon concentration.

In yet another preferred implementation of the present invention, the water parameter sensor(s) measure total PFAS concentration.

In one preferred implementation of the present invention, the water parameter sensor(s) measure total heavy metal concentration.

In a preferred embodiment of the present invention, the smart water meter further comprises an ultra-violet light source, an ozone generator, a particulate filter, and/or a flow diverted.

BRIEF DESCRIPTION OF THE DRAWINGS

Certain embodiments of the present invention are illustrated by the accompanying figures. It will be understood that the figures are not necessarily to scale and that details not necessary for an understanding of the invention or that render other details difficult to perceive may be omitted.

It will be further understood that the invention is not necessarily limited to the particular embodiments illustrated herein.

Figure 1:
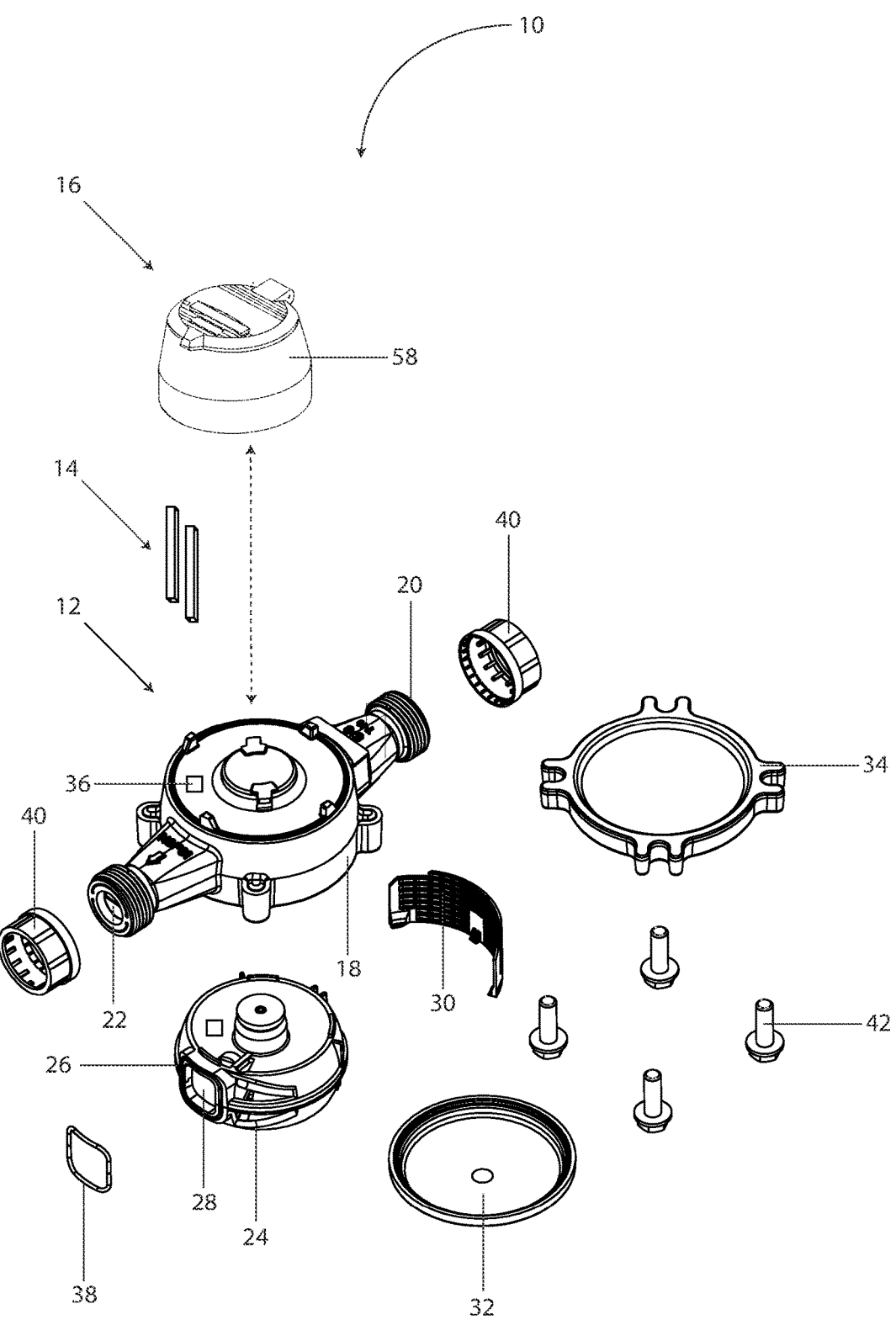
Figure 2:
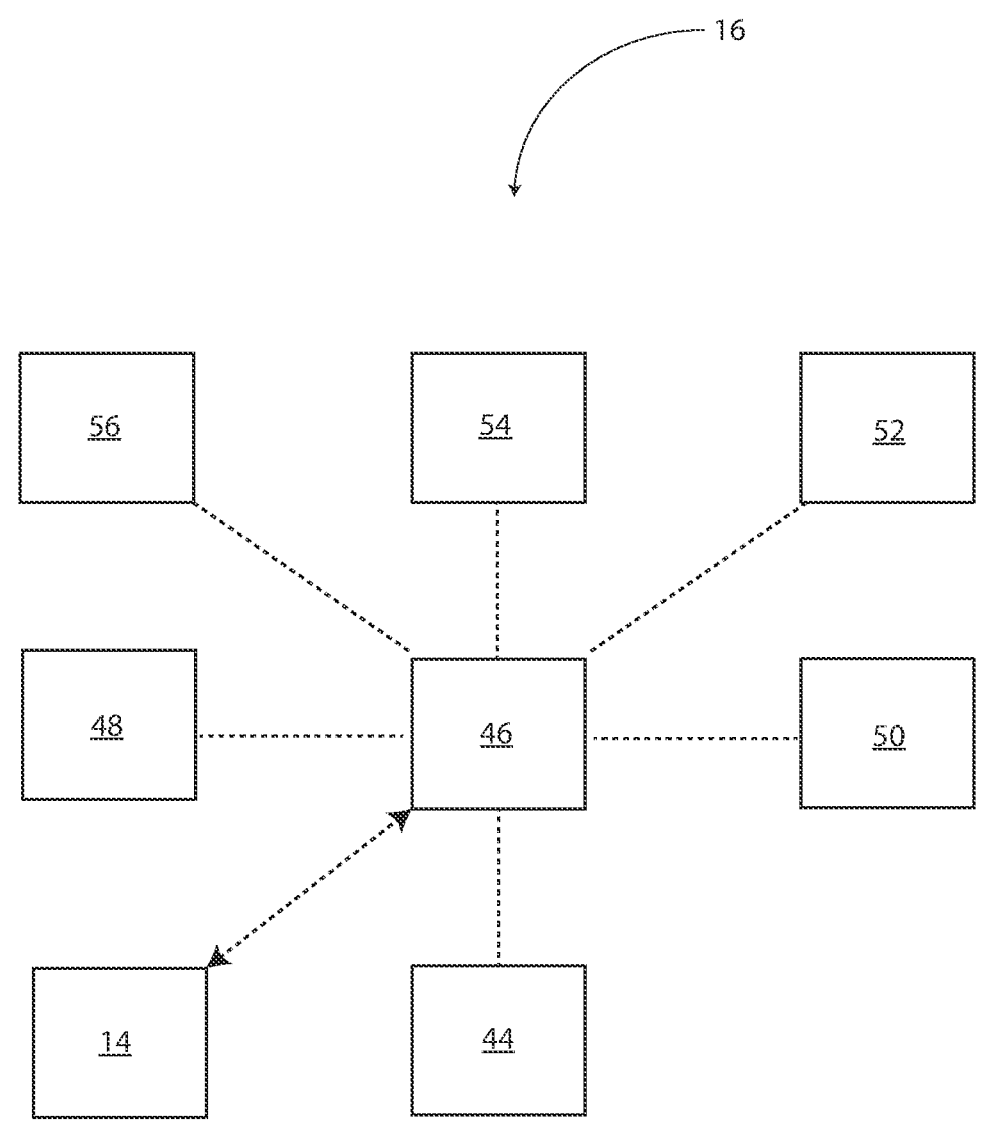
Figure 3:
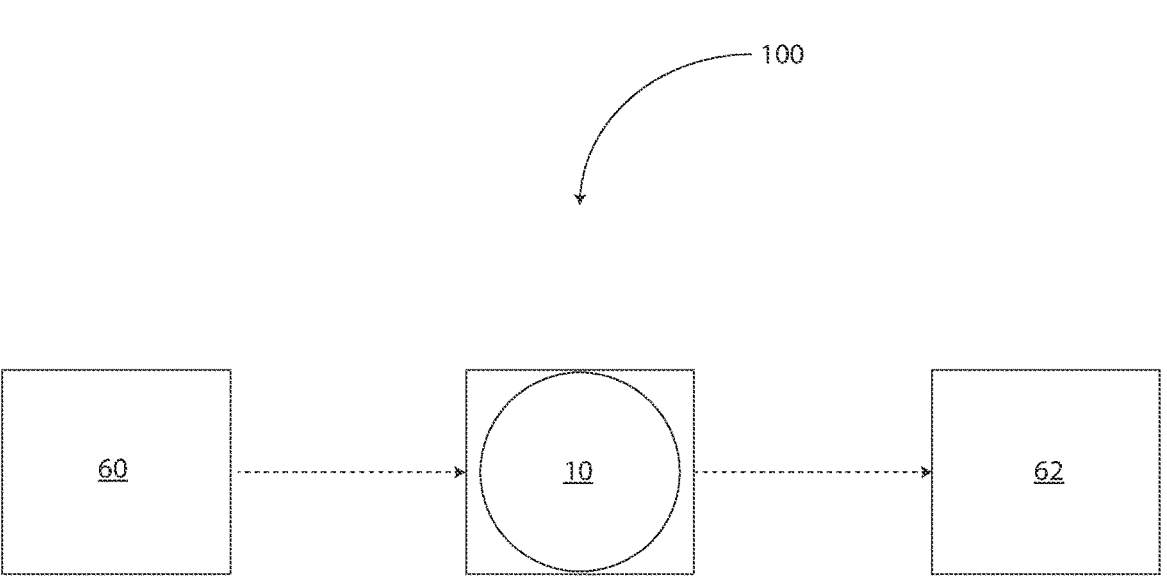
Figure 4:
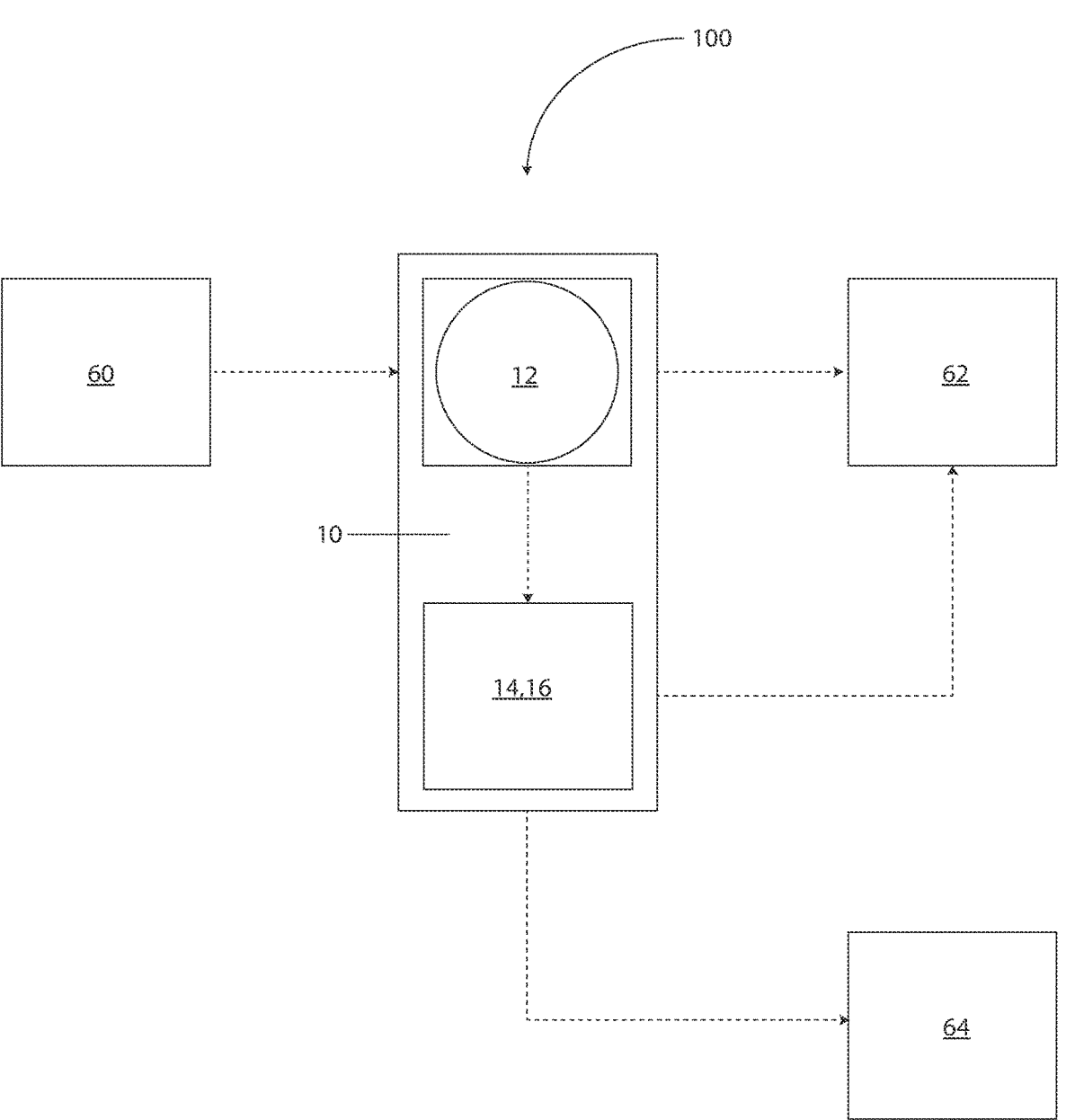

The invention will now be described with reference to the drawings wherein:

FIG. 1 of the drawings is an exploded perspective view of a smart water meter of the present invention;

FIG. 2 of the drawings is schematic representation of a data transmission/electronics assembly for use in accordance with smart water meters of the present invention;

FIG. 3 of the drawings is schematic representation of a smart water meter associated with a water main and a consumer's residence; and FIG. 4 of the drawings is schematic representation of a smart water system of the present invention.

DETAILED DESCRIPTION OF THE INVENTION

While this invention is susceptible of embodiment in many different forms and applications, there are shown in the drawings and described herein in detail several specific embodiments with the understanding that the present disclosure is to be considered as an exemplification of the principles of the invention and is not intended to limit the invention to the embodiments illustrated.

It will be understood that like or analogous elements and/or components, referred to herein, may be identified throughout the drawings by like reference characters. In addition, it will be understood that the drawings are merely schematic representations of one or more embodiments of the invention, and some of the components may have been distorted from their actual scale for purposes of pictorial clarity.

In accordance with the present invention, the smart water meters disclosed herein provide peace of mind to the consumer that there are no water leaks and/or that the water being utilized and/or consumed is safe and well within predetermined parameters or limits. These limits monitor, for example, heavy metal contamination (e.g., lead, arsenic, mercury, etcetera), PFAS contamination, hydrocarbon contamination, and viral, bacterial, fungi contamination, pesticides, herbicides, and/or fungicides—just to name a few. Preferably, the smart water meters of the present invention record, store, and report historical water quality data. The smart water meters of the present invention also measure and/or monitor water flow rates and/or water consumption over one or more periods of time. This allows for leak detection and water consumption analysis. In addition, the smart water meters preferably alert the consumer and/or municipality if a water leak and/or water flow irregularity (e.g., backflow, clog, etcetera) is detected and/or if the water quality is outside of predetermined, safe parameters (e.g., the presence of lead, mercury, heavy metals, hydrocarbons, pesticides, herbicides, fungicides and per- and/or polyfluoroalkyl substances (PFAS).

Referring now to the drawings, and to FIG. 1 in particular, a first embodiment of smart water meter 10, is shown as generally comprising water flow measuring assembly 12, one or more water parameter sensors/probes/detectors 14, and data transmission assembly 16.

Water flow measuring assembly 12 preferably comprises housing 18, water input 20, water output 22, water flow measuring chamber 24, thrust roller 26, diaphragm 28, strainer 30, gasket/liner 32 for bottom cap 34, housing sensor throughput/aperture 36, O-ring 38, spud caps 40, and bolts/fasteners 42. Other water flow measuring assemblies and components therefore are also contemplated for use in accordance with the present invention, including, for example, those disclosed in United States Patent Application Publication Number 2011/0219870 entitled "Unitary Drive System for Water Meter," and U.S. Pat. No. 6,948,363 entitled "Disc Metering Assembly for Resisting Rotational Forces"—all of which are hereby incorporated herein by reference in their entirety including all references cited therein.

Smart water meter 10 includes one or more water parameter sensors/probes/detectors 14. The sensors of the present invention preferably monitor water temperature, potential of hydrogen (pH), turbidity, transmissivity, conductance, the concentration of dissolved oxygen in the water, the concentration of blue-green algae (cyanobacteria) in the water, the concentration of chlorophyll in the water, the concentration of colored dissolved organic matter (CDOM) in the water, the total cation, anion, and/or ion concentration, the total hydrocarbon concentration, the total PFAS concentration, and/or the total heavy metal concentration. Water parameter sensors of the present invention are commercially available from Eureka Water Probes (Austin, Texas) and Hach (Loveland, Colorado). Sensors 14 may be associated with water flow measuring assembly 12 inline via throughput aperture 36, or, alternatively, sensors 14 may be configured in a bypass loop that is offline and preferably regulated via a pair of flow controls/valves (not shown).

Data transmission assembly 16 is associated with both water flow measuring assembly 12 and sensors 14, and records, stores, and reports historical water quality data and/or alerts the consumer and/or municipality if a water leak and/or water flow irregularity (e.g., backflow, clog, etcetera) is detected and/or if the water quality is outside of predetermined, safe parameters.

Referring now to FIG. 2, data transmission/electronics assembly 16 of smart water meter 10 is in bilateral communication with sensors 14, and generally comprises energy source 44, circuit board/controller (e.g., printed circuit board) 46, primary user interface 48, memory module 50, communications module 52, light source/speaker/display 54, and CMOS sensor 56.

Energy source 44 is preferably at least partially contained within housing 58 of data transmission/electronics assembly 16. Energy source 44 is also preferably in electrical communication with circuit board 46, and/or communications module 52, light source/speaker/display 54, and/or CMOS sensor 56. Energy source 44 of the electronics assembly preferably comprises, for example, an AC power supply, a DC power supply, an AC-DC power supply, a primary electrochemical cell, a secondary electrochemical cell, and/or a fuel cell.

Circuit board/controller 46 is preferably at least partially contained within housing 58 of data transmission/electronics assembly 16. Circuit board/controller 46 is preferably in electrical communication with energy source 44, primary user interface 48, memory module 50, communications module 52, light source/speaker/display 54, and CMOS sensor 56.

In a preferred embodiment of the present invention, circuit board/controller 46 of electronics assembly 16 comprises one or more components, such as a battery, a bridge rectifier, a capacitor, a central processing unit, a communications port, a control board, a crystal, a diode, a fuse, a graphics board, an inductor, an input port, an integrated circuit, a microprocessor, a memory module, an oscillator, an output port a potentiometer, a receiver, a relay, a resistor, a semiconductor, a transformer, a transistor, a tuner, a video processing unit, a wired communications hub, and/or a wireless communications hub.

Primary user interface 48 is preferably associated with at least one of the sidewalls, and the top wall of housing 58. Primary user interface 48 is preferably in electrical communication with circuit board/controller 46.

Memory module 50 is preferably associated with and/or contained in housing 58 of data transmission/electronics assembly 16. Memory module 50 is preferably in electrical communication with circuit board/controller 46, and records, stores, and reports historical data from sensors 14.

Communications module 52 is preferably associated with and/or contained in housing 58 of data transmission/electronics assembly 16. Communications module 52 is preferably in electrical communication with circuit board/controller 46, and can communicatively couple with a customer's and/or municipality's computers systems and networks over a wired or wireless connection, as would be known to one of ordinary skill in the art.

Component 54 may comprise one or more of a light source, a speaker, and a display. Component 54 of transmission/electronics assembly 16 is preferably at least partially contained within housing 58 of data transmission/electronics assembly 16. Component 54 is preferably in electrical communication with circuit board/controller 46. Component 54 is capable of providing an audio and/or a visual alert at the site of the water meter in the event that a leak and/or fault is detected.

In another embodiment of the present invention, data transmission/electronics assembly 16 further comprises one or more of a secondary energy source, a secondary light source, a secondary user interface, a secondary circuit board, a secondary speaker, a vibration mechanism, a white noise generator, a thermo sensor, a tactile sensor, and/or a display—all of which are preferably in electrical communication with circuit board/controller 46. Preferably, the display is adapted to display at least one of alpha-numeric content, temperature, time, image and/or graphic.

In a preferred embodiment of the present invention, data transmission/electronics assembly 16 further comprises an image sensor that is in electrical communication with the circuit board. The image sensor preferably provides a user with an image (e.g., a photo, a video) associated with the area proximate smart water meter 10. Examples of suitable image sensors include video camera tubes, semiconductor charge-coupled devices (CCD), active pixel sensor in complementary metal-oxide-semiconductors (CMOS), N-type metal-oxide-semiconductors (NMOS, Live MOS), and back-side illuminated complementary metal-oxide-semiconductors (BSI-CMOS).

It will be understood that the above-identified image sensors are commercially available from a plurality of sources, including Agilent, Aptina, Canesta, Canon, Caeleste, CMOSIS, Dalsa, Eastman Kodak, ESS Technology, Fujifilm, MagnaChip, Matsushita, MAZeT GmbH, Mitsubishi, Nikon OmniVision Technologies, ON Semiconductor, Cypress Semiconductor, PixArt Imaging, Pixim, Samsung, Sharp, Sony, STMicroelectronics, Toshiba, TowerJazz, Town Line Technologies, TransChip, Trusight and Trusense Imaging—just to name a few suppliers.

Additional examples of suitable image sensors for use in accordance with the present invention include U.S. Pat. No. 6,359,323 B1 entitled "Color image sensor and method for fabricating the same," United States Patent Application Publication No. 2006/0043261 A1 entitled "Solid state image pickup device and image pickup system comprising it," U.S. Pat. No. 7,129,979 B1 entitled "Image sensor pixel for global electronic shuttering," United States Patent Application Publication No. 2004/0147059 A1 entitled "Method for manufacturing CMOS image sensor having microlens therein with high photosensitivity," U.S. Pat. No. 5,990,506 A entitled "Active pixel sensors with substantially planarized color filtering elements," U.S. Pat. No. 6,235,549 B1 entitled "Method and apparatus for employing a light shield to modulate pixel color responsivity," U.S. Pat. No. 6,765,276 B2 entitled "Bottom antireflection coating color filter process for fabricating solid state image sensors," U.S. Pat. No. 6,486,913 B1 entitled "Pixel array with shared reset circuitry," U.S. Pat. No. 6,872,584 B2 entitled "Solid state image sensor and method for fabricating the same," United States Patent Application Publication No. 2006/0011813 A1 entitled "Image sensor having a passivation layer exposing at least a main pixel array region and methods of fabricating the same," United States Patent Application Publication No. 2007/0187793 A1 entitled "Filter, color filter array, method of manufacturing the color filter array, and image sensor," U.S. Pat. No. 6,379,992 B2 entitled "Method for fabricating an image sensor," United States Patent Application Publication No. 2006/0138500 A1 entitled "CMOS image sensor and method for fabricating the same," United States Patent Application Publication No. 2005/0263839 A1 entitled "Photoelectric converting film stack type solid-state image pickup device, and method of producing the same," United States Patent Application Publication No. 2007/0090274 A1 entitled "Image sensors including active pixel sensor arrays," United States Patent Application Publication No. 2006/0157761 A1 entitled "Image sensor with self-boosting and methods of operating and fabricating the same," U.S. Pat. No. 6,369,417 B1 entitled "CMOS image sensor and method for fabricating the same," U.S. Pat. No. 6,127,668 A entitled "Solid state image pickup device and method for manufacturing the same," United States Patent Application Publication No. 2007/0023802 A1 entitled "CMOS image sensor and method of fabricating the same," United States Patent Application Publication No. 2005/0090035 A1 entitled "Method for fabricating CMOS image sensor protecting low temperature oxide delamination," and United States Patent Application Publication No. 2006/0261342 A1 entitled "Imaging device having a pixel cell with a transparent conductive interconnect line and the method of making the pixel cell"—all of which are hereby incorporated herein by reference in their entirety, including all references cited therein.

In a preferred embodiment of the present invention, smart water meter 10 further comprises an ultra-violet light source, an ozone generator, a particulate filter, and/or a flow diverter.

As is shown in FIG. 3, water system 100 includes smart water meter 10 that can be associated with water main 60, in an inline configuration, with consumer's residence 62. In this configuration, water meter 10 is capable of recording, storing, and locally and/or remotely reporting historical water data and/or when a predetermined water quality limit is breached. Such data collection occurs simultaneously and in real time. In one implementation, smart water meter 10 can isolate consumer's residence 62 from water main 60 if, for example, a water leak is detected. Such a detection includes, but is not limited to, high flow rates (e.g., water pipe breaking) exceeding a predetermined rate and/or long-term, low and continuous flow rate (e.g., leaking toilet or sink left on). Isolation preferably occurs via a shut-off valve that is mechanically and/or electro-mechanically operated. It will be understood that smart water meter 10, may also be in-line between water main 60 and, for example, an appliance, icemaker, a dishwasher, a toilet, a sink, hot water heater, well, water filter, and/or another water consuming, displacing, and/or containing device within or around the consumer's residence. These meters can be localized or form part of an overall smart water system. A localized meter may include a water inlet, a water outlet, a flow sensor, and an isolator or shut-off valve and/or any additional components disclosed herein. This enables localized and/or global integration of one or more smart water meters.

As is shown in FIG. 4, water system 100 includes smart water meter 10 that can be associated with water main 60, in a bypass configuration, with consumer's residence 62. In this configuration, water meter 10 is capable of recording, storing, and locally and/or remotely reporting historical water data and/or when a predetermined water quality limit is breached. Such data collection occurs simultaneously and in real time. When a breach is identified water can be diverted to sewer/reservoir 64 so that the consumer is not exposed to water that is unsafe for human consumption and/or exposure.

The foregoing description merely explains and illustrates the invention and the invention is not limited thereto except insofar as the appended claims are so limited, as those skilled in the art who have the disclosure before them will be able to make modifications without departing from the scope of the invention.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etcetera shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etcetera. As a non-limiting example, each range discussed herein can be readily broken down into a lower third, middle third and upper third, etcetera. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed and desired to be secured by Letters Patent of the United States is:

1. A smart water meter, comprising:
   a water flow measuring assembly configured to measure a volume of water flowing through the smart water meter;
   at least one water parameter sensor configured to sense one or more parameters of water flowing through the smart water meter, wherein the at least one water parameter sensor measures water transmissivity; and
   a data transmission assembly configured to wirelessly transmit data, wherein the data transmission assembly compares measured water parameter data against predetermined threshold values and automatically transmits an alert to a consumer when a measured parameter deviates from a predetermined threshold value,
   wherein the smart water meter validates and provides alerts to a consumer and/or municipality if a water leak and/or water flow irregularity is detected and/or if the water quality is outside of predetermined, safe parameters.

2. The smart water meter according to claim 1, wherein the smart water meter records, stores, and reports historical water quality data and/or water flow rates and/or water consumption over one or more periods of time.

3. The smart water meter according to claim 1, wherein the at least one water parameter sensor measures total heavy metal concentration.

4. The smart water meter according to claim 1, wherein the water flow measuring assembly comprises a housing, a water input, a water output, and a water flow measuring chamber.

5. The smart water meter according to claim 1, wherein the at least one water parameter sensor measures water temperature.

6. The smart water meter according to claim 1, wherein the at least one water parameter sensor measures potential of hydrogen (pH).

7. The smart water meter according to claim 1, wherein the at least one water parameter sensor measures water turbidity.

8. The smart water meter according to claim 1, wherein the at least one water parameter sensor measures total PFAS concentration.

9. The smart water meter according to claim 1, wherein the at least one water parameter sensor measures conductance of the water.

10. The smart water meter according to claim 1, wherein the at least one water parameter sensor measures the concentration of dissolved oxygen in the water.

11. The smart water meter according to claim 1, wherein the at least one water parameter sensor measures the concentration of blue-green algae (cyanobacteria) in the water.

12. The smart water meter according to claim 1, wherein the at least one water parameter sensor measures the concentration of chlorophyll in the water.

13. The smart water meter according to claim 1, wherein the at least one water parameter sensor measures the concentration of colored dissolved organic matter (CDOM) in the water.

14. The smart water meter according to claim 1, wherein the at least one water parameter sensor measures total cation concentration.

15. The smart water meter according to claim 1, wherein the at least one water parameter sensor measures total anion concentration.

16. The smart water meter according to claim 1, wherein the at least one water parameter sensor measures total hydrocarbon concentration.

17. A smart water meter system, comprising:
   a water flow measuring assembly comprising a housing with a water input, a water output, and a water flow measuring chamber, wherein the smart water meter records, stores, and reports historical water quality data and/or water flow rates and/or water consumption over one or more periods of time;
   at least one water parameter sensor configured in a bypass loop that is offline from the water flow measuring assembly and regulated via a pair of flow control valves; and
   a data transmission assembly configured for wireless communication,
   wherein the data transmission assembly automatically transmits real-time leak detection alerts to both a local consumer device and a remote municipality monitoring system, said alerts including leak location data, flow rate deviation data, and timestamp information, and
   wherein the smart water meter alerts the consumer and/or municipality if a water leak and/or water flow irregularity is detected outside of predetermined safe parameters.

\* \* \* \* \*